United States Patent
Simon

(10) Patent No.: US 8,340,376 B2
(45) Date of Patent: Dec. 25, 2012

(54) DIFFUSION TENSOR IMAGING CONFIDENCE ANALYSIS

(75) Inventor: David A. Simon, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1294 days.

(21) Appl. No.: 12/047,004

(22) Filed: Mar. 12, 2008

(65) Prior Publication Data

US 2009/0232374 A1    Sep. 17, 2009

(51) Int. Cl.
*G06T 7/40* (2006.01)
(52) U.S. Cl. .......................................... 382/128
(58) Field of Classification Search .................... 382/128
See application file for complete search history.

(56) References Cited

U.S. PATENT DOCUMENTS

| | | |
|---|---|---|
| 5,539,310 A | 7/1996 | Basser et al. |
| 5,592,939 A | 1/1997 | Martinelli |
| 5,913,820 A | 6/1999 | Bladen et al. |
| 5,969,524 A | 10/1999 | Pierpaoli et al. |
| 6,381,485 B1 | 4/2002 | Hunter et al. |
| 6,474,341 B1 | 11/2002 | Hunter et al. |
| 6,526,305 B1 | 2/2003 | Mori |
| 6,624,632 B2 | 9/2003 | Iriguchi et al. |
| 6,670,812 B1 | 12/2003 | Mock et al. |
| 6,704,698 B1* | 3/2004 | Paulsen et al. .................. 704/1 |
| 6,806,705 B2 | 10/2004 | van Muiswinkel et al. |
| 6,845,342 B1 | 1/2005 | Basser et al. |
| 6,859,203 B2 | 2/2005 | van Muiswinkel et al. |
| 6,891,373 B2 | 5/2005 | Deimling |
| 6,969,991 B2 | 11/2005 | Bammer et al. |
| 6,992,484 B2 | 1/2006 | Frank |
| 2002/0042569 A1* | 4/2002 | Wedeen ........................ 600/411 |
| 2004/0152970 A1* | 8/2004 | Hunter et al. ................. 600/424 |
| 2004/0215071 A1 | 10/2004 | Frank et al. |
| 2007/0127794 A1* | 6/2007 | Niogi et al. ................... 382/128 |
| 2007/0249911 A1 | 10/2007 | Simon |
| 2008/0064947 A1* | 3/2008 | Heruth et al. ................. 600/407 |

FOREIGN PATENT DOCUMENTS

WO   WO-03062859 A1   7/2003
WO   WO-2005076030 A1   8/2005

OTHER PUBLICATIONS

"Diffusion Tensor Imaging," Scientific Computing and Imaging Institute. 2 pages. http://www.sci.utah.edu/research/diff-tensor-imaging.html. Web. Accessed Aug. 11, 2006.

(Continued)

*Primary Examiner* — Robert Kim
*Assistant Examiner* — Eliza Osenbaugh-Stewart
(74) *Attorney, Agent, or Firm* — Harness, Dickey

(57) ABSTRACT

A system and method can increase confidence or other factors of a tract identified in a selected image data. The system can use various confidence determining factors to identify confidence in the identified tract. The identified tract can be used for various purposes, such as diagnosis or treatment.

45 Claims, 4 Drawing Sheets

OTHER PUBLICATIONS

"Diffusion-Weighted Imaging." This article was formerly located on the World Wide Web at http://spinwarp.ucsd.edu/NeuroWeb/Text/br-710dwi.htm but which currently automatically redirects to the University of Southern California at San Diego (USCSD) Center for Functional MRI located at http://fmri.ucsd.edu/. The attached non-patent literature article for "Diffusion-Weighted Imaging" was printed from the Wayback Machine web archive at: http://web.archive.org/web/20060902144543/http://spinwarp.ucsd.edu/NeuroWeb/Text/br-710dwi.htm from the time period of Sep. 2, 2006. (Web Wayback Machine archive accessed and printed Dec. 3, 2010.).

Alexander, D.C., C. Pierpaoli, P.J. Basser, and J.C. Gee. (Nov. 2001) Spatial transformations of diffusion tensor magnetic resonance images. IEEE transactions on medical imaging, 20: 1131-1139.

Anderson, A.W. (2001) Theoretical analysis of the effects of noise on diffusion tensor imaging. Magnetic Resonance in Medicine 46: 1174-1188.

Bammer, R., B. Acar, M.E. Moseley, 2003. In vivo MR tractography using diffusion imaging. European Journal of Radiology 45: 223-234.

Basser, P.J. and D.K. Jones. (2002) Review Article: Diffusion-tensor MRI: theory, experimental design and data analysis—a technical review. NMR in Biomedicine 15: 456-467.

Basser, P.J., Pierpaoli, C. (1994) Estimation of the effective self-diffusion tensor from the NMR spin echo. J. Magn. Reson., Ser. B 111, 209-219.

Basser, P.J., S. Pajevic, C. Pierpaoli, J. Duda, and A. Aldroubi, 2000. In vivo fiber tractography using DT-MRI data. Magnetic Resonance in Medicine 44:625-632.

Berman, J., et al. (Jul. 2004) Diffusion-tensor imaging—guided tracking of fibers of the pyramidal tract combined with intraoperative cortical stimulation mapping in patients with gliomas. J Neurosurg 101:66-72.

Chou, M-C., Y-R. Lin, T-Y Huang, C-Y Wang, H-W Chung, C-J Juan, C-Y Chen. (Mar. 2005) FLAIR diffusion-tensor MR tractography: comparison of fiber tracking with conventional imaging. American Journal of Neuroradiology 26: 591-597.

Clark, C.A., Barker, G. J., Toffs, P.S. (1999) Magnetic resonance diffusion imaging of the human cervical spinal cord in vivo. Magn. Reson. Med. 41, 1269-1273.

Clayden, Jonathan D., et al. (2006) Improved segmentation reproducibility in group tractography using a quantitative tract similarity measure. NeuroImage 33:482-492.

Coenen, V.A., et al. (2001) Three-dimensional visualization of the pyramidal tract in a neuronavigation system during brain tumor surgery: first experiences and technical note. Neurosurgery 49 (1), 86-93.

Conturo, T.E., N.F. Lori, T.S. Cull, E. Akbudak, A. Z. Snyder, J.S. Shimony, R.C. McKinstry, H. Burton, M.E. Raichle. (Aug. 1999) Tracking neuronal fiber pathways in the living human brain. Proc. Natl. Acad. Sci, V96:10422-10427.

DaSilva, A.F.M., D.S. Tuch, M.R. Wiegell, and N. Hadjukhani. (Jul. 2003) A primer on diffusion tensor imaging of anatomical substructures. Neurosurg Focus 15(1): Article 4, pp. 1-4.

Ehricke, Hans-H., et al. (2006) Visualizing MR diffusion tensor fields by dynamic fiber tracking and uncertainty mapping. Computers & Graphics 30:255-264.

International Preliminary Report on Patentability and Written Opinion mailed Sep. 23, 2010 for PCT/US2009/036776 which claims benefit of U.S. Appl. No. 12/047,004, filed Mar. 12, 2008.

International Search Report and Written Opinion mailed Sep. 10, 2010 for PCT/US2009/036776 which claims benefit of U.S. Appl. No. 12/047,004, filed Mar. 12, 2008.

Jellison, B.J., A. S. Field, J. Medow, M. Lazar, M.S. Salamat, A.L. Alexander. (Mar. 2004) Diffusion tensor imaging of cerebral white matter: a pictorial review of physics, fiber tract anatomy, and tumor imaging patterns. Am J Neuroradiol 25: 356-369.

Jones, Derek K., et al. (2005) Confidence Mapping in Diffusion Tensor Magnetic Resonance Imaging Tractography Using a Bootstrap Approach. Magnetic Resonance in Medicine 53:1143-1149.

Lazar, M. (2003) White Matter Tractography: An Error Analysis and Human Fiber Tract Reconstruction Study. Doctoral Dissertation, University of Utah. http://brainimaging.waisman.wisc.edu/~mlazar/Other_information.html. Said url is no longer valid. The article can be found using the Wayback Machine archive at: http://web.archive.org/web/20060828071630/http://brainimaging.waisman.wisc.edu/~mlazar/Other_information.html. Accessed and printed Dec. 6, 2010.

Lazar, M., and A. Alexander, 2006. Characterizing uncertainty in tractography: parametric and nonparametric methods. 2006 IEEE International Symposium on Biomedical Imaging: From Nano to Macro. Apr. 6-9, 2006, Arlington, VA.

Lazar, M., and A. Alexander. (2001) Error Analysis of White Matter Tracking Algorithms (Streamlines and Tensorlines) for DT-MRI. Proc. Intl. Soc. Mag. Reson. Med. 9: 506.

Lazar, M., and A.L. Alexander. (2003) An error analysis of white matter tractography methods: synthetic diffusion tensor field simulations. NeuroImage 20: 1140-1153.

Lazar, M., D.M. Weinstein, J.S. Tsuruda, K.M. Hasan, K. Arfanakis, M.E. Meyerand, B. Badie, H.A. Rowley, V. Haughton, A. Field, A.L. Alexander, 2003. White matter tractography using diffusion tensor deflection. Human Brain Mapping 18:306-321.

LeBihan, D., et al. (1986) MR imaging of intravoxel incoherent motions: applications to diffusion and perfusion in neurological disorders. Radiology 161, 401-407.

LeBihan, D., J-F. Mangin, C. Poupon, C.A. Clark, S. Pappata, N. Molko, H. Chabriat, (2001) Diffusion tensor imaging: concepts and applications. Journal of Magnetic Resonance Imaging 13: 534:546.

Lori, N. F., et al. (2002) Diffusion tensor fiber tracking of human brain connectivity: aquisition methods, reliability analysis and biological results. NMR in Biomedicine 15:493-515.

Maier, S. E., M.E. Shenton, F.A. Jolesz, 2001. Diffusion MRI explores new indications. A Special Supplement to Diagnostic Imaging. CMP Medica, LLC.

Mori, S., and P.C.M. van Zijl. (Dec. 2002) Review article fiber tracking: principles and strategies—a technical review. NMR in Biomedicine 15:468-480.

Mori, S., B.J. Crain, V.P. Chacko, P.C.M. van Zijl, 1999. Three-dimensional tracking of axonal projections in the brain by magnetic resonance imaging. Ann Neurol 45: 265-269.

Mori, S., et al. (2002) Imaging cortical association tracts in the human brain using diffusion-tensor-based axonal tracking. Magn Reson Med 47:215-223.

Moseley, M.E., et al. (1990) Diffusion-weighted MR imaging of anisotropic water diffusion in cat central nervous system. Radiology 176:439-445.

Mukherjee, P., J.H. Miller, J.S. Shimony, J.V. Philip, D. Nehra, A.Z. Snyder, T.E. Conturo, J.J. Neil, and R.C. McKinstry, 2002. Diffusion-Tensor MR imaging of gray and white matter development during normal human brain maturation. Am. J. Neuroradiol 23:1445-1456.

Pajevic, S. and P.J. Basser, 2003. Parametric and non-parametric statistical analysis of DT-MRI data. Journal of Magnetic Resonance 161: 1-14.

Piearpoli, C., et al. (1996) Diffusion tensor MR imaging of the human brain. Radiology 201, 637-648.

Scollan, D.F., A. Holmes, R. Winsolow, and J. Forder. (1998) Histological validation of myocardial microstructure obtained from diffusion tensor magnetic resonance imaging. Am. J. Physiology V. 275, pp. H2308-H2318.

Sen, Pabitra N., et al., (2005) Modeling diffusion in white matter in the brain: A composite porous medium. 23: 215-220.

Stieltjes, B., et al.. (2001) Diffusion Tensor Imaging and Axonal Tracking in the Human Brainstem. NeuroImage 14, 723-735.

Tournier, J-D., F. Calamante, M.D. King, D.G. Gadian, and A. Connelly, 2002. Limitations and requirements of diffusion tensor fiber tracking: an assessment using simulations. Magnetic Resonance in Medicine 47: 701-708.

Tournier, J.-Donald, et al. (2004) Direct estimation of the fiber orientation density function from diffusion-weighted MRI data using spherical deconvolution. NeuroImage 23:1176-1185.

vanGelderen, P., H.M. deVleeschouwer, D. DesPres, J. Pekar, P.C. van Zijl, C.T.W Moonen. Water diffusion and acute stroke. Magn. Reson. Med. 31: 154-163.

Westin, C-F., S. Peled, H. Gudbjartsson, R. Kikinis, F.A. Jolesz. (1997) Geometrical diffusion measures for MRI from tensor basis analysis. ISMRM'97, Vancouver, Canada, p. 1742.

Wiegell, M.R., H.B.W. Larsson, V.J. Wedeen. (2000) Fiber crossing in human brain depicted with diffusion tensor MR imaging. Radiology 217:897-903.

Zhang, S., C. Demiralp, and D.H. Laidtaw. (2003) Visualizing diffusion tensor MR images using streamtubes and stream surfaces. IEEE Transactions on Visualization and Computer Graphics V.9, No. 4, pp. 454-462.

Zhang, S., et al., "Diffusion Tensor MRI Visualization." The Visualization Handbook. May 24, 2004 pp. 317-330.

Mori, S., et al. "MRI Atlas of Human White Matter." (2005) Elsevier, B.V., Amsterdam, The Netherlands. pp. 1-31.

* cited by examiner

DIFFUSION TENSOR IMAGING CONFIDENCE ANALYSIS

FIELD

The present teachings relate generally to an imaging system, and particularly to an analysis system for diffusion imaging of an anatomy.

BACKGROUND

The statements in this section merely provide background information related to the present disclosure and may not constitute prior art.

Imaging techniques have been used to image various portions of the human anatomy. Imaging techniques include ionizing radiation, producing fields relative to a human anatomy, etc. For example, x-ray imaging techniques include directing radiation through an anatomy and receiving a selected portion of the radiation on a film or collecting surface. Other types of imaging include producing fields relative to an anatomy, such as a magnetic field (e.g. magnetic resonance imager (MRI)), and sensing a change in atomic particles of the anatomy induced by the fields.

Various techniques can be used to acquire information relating to an anatomy, such as a human anatomy. For example, a MRI, which uses magnetic fields and radio frequency energy, can be used to acquire information regarding diffusion of various components or matter within the anatomy, such as water. Matter, such as water, can diffuse in the anatomy according to various principles, including Brownian motion. Diffusion can be anisotropic or isotropic. Anisotropic diffusion is generally along a selected path based upon restrictions on movement of the water, such as due to muscle fibers, fiber tracts in the brain, or other features. The anisotropic movement of the water can be defined based upon a tensor defining the motion or average motion of water within a voxel being imaged with a MRI. The MRI can be used to detect or determine the diffusion based on an attenuation of the MRI signal due to the diffusion of the water. Further analysis or processing can be used to determine a tensor based upon the movement of the water as it diffuses over time. Quick successive pulses of a MRI system can be used acquire data to determine the movement of water. The tensor can be used to determine information regarding the data, such as an Eigenvalue or Eigenvector, relating to the movement. The Eigenvector can define the average movement of water within a selected voxel of the MRI data. A more detailed discussion of DTI data acquisition and processing is discussed in Bihan et al., Diffusion Tensor Imager: Concept and Applications, Journal and Magnetic Resonance Imaging, 13, 534-546 (2001).

As discussed above, diffusion data from a MRI can be used to determine movement of water and the information can be used to illustrate the movement of the water on image data. The movement of water within a particular voxel can also be used to identify selected anatomical structures, such as fiber tracts. Various algorithms or techniques can be used to identify fiber tracts within the anatomy. Diffusion tensor image data, however, is substantially non-invasive and the tract developed based on the data includes only a certain amount of confidence.

SUMMARY

A method and system is taught that allows for increased sensitivity, increased confidence, and other factors relative to diffusion image data of a selected region. In particular, various techniques can be used to develop or determine a confidence of an identified tract in an anatomy based upon the DTI data. DTI data can be used to extrapolate or determine fiber tracts and anatomical structures based on various processes, such as tractography. Various algorithms can be used to define tracts in an anatomy and a confidence value can be determined for a particular identified tract. For example, perturbation of an initial determination can be used to insure an appropriate mapping of a venous or flow system.

According to various embodiments a method to determine a confidence in a displayed image data of an anatomy is taught. The method can include obtaining image data of the anatomy including data regarding diffusion of a liquid. A first estimate of an anatomical structure and a second estimate of the anatomical structure based upon the obtained image data can be made. The first estimate of the anatomical structure and the second estimate of the anatomical structure can also be compared.

According to various embodiments a method of determining a confidence in a displayed image data of an anatomy is taught. The method can include obtaining a gradient image data of the anatomy and determining a diffusion of water with the gradient image data of the anatomy including formulating a tensor of the diffusion. A first starting portion in the obtained image data can be determined and a first estimate of an anatomical structure can be made. A second starting portion in the obtained image data can be determined and a second estimate of the anatomical structure can be determined. A confidence of the determined first estimate of the anatomic structure can also be determined.

According to various embodiments a method of determining a confidence in a displayed image data of an anatomy is taught. The method can include obtaining gradient image data of the anatomy and determining a diffusion of water with the gradient image data of the anatomy including formulating a tensor of the diffusion. A first criterion can be selected in the image data and a first estimate of an anatomical structure can be made based at least in part on the selected first criterion. A second criterion can be selected and a second estimate of the anatomical structure can be made based at least in part on the selected second criterion. The first estimate of the anatomical structure and the second estimate of the anatomical structure can be compared. A difference between the first estimate of the anatomical structure and the second estimate of the anatomical structure can be determined. A configuration of the anatomical structure can be determined and a confidence in the determined configuration of the anatomical structure can be made based at least in part on the determined difference between the first estimate of the anatomical structure and the second estimate of the anatomical structure.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
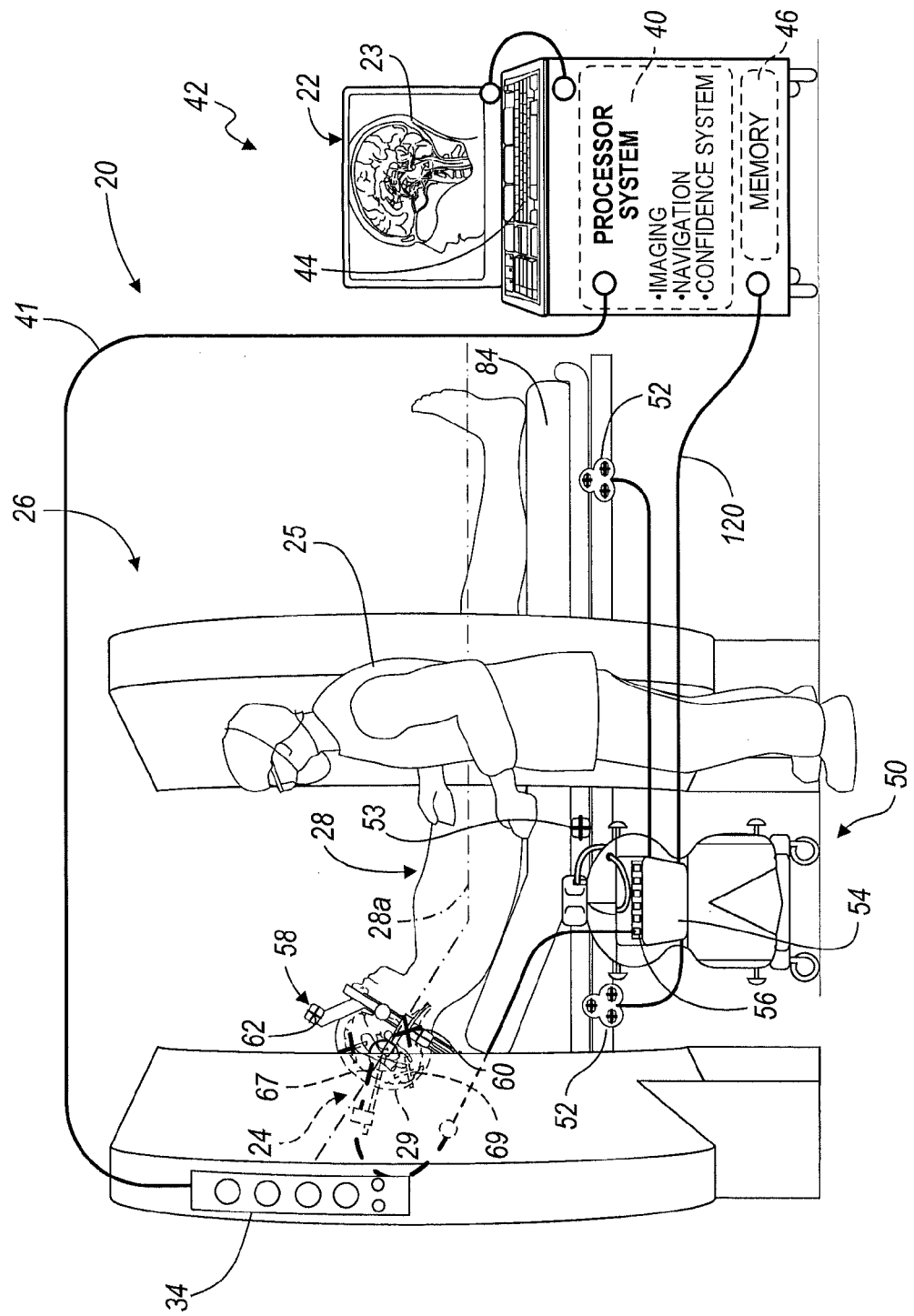
FIG. 1 is an environmental view of a surgical navigation system according to various embodiments.

A guided procedure can be performed with a navigation system 20, illustrated in FIG. 1. The guided procedure can be any appropriate procedure, such as a neural procedure, spinal procedure, and orthopedic procedure. The navigation system 20 can include various components, as will be discussed further herein. The navigation system 20 can allow a user, such as a surgeon to view on a display 22 a relative position of an instrument 24 to a coordinate system. The coordinate system can be made relative to an image, such as in an image guided procedure, or can be registered to a patient only, such as in an imageless procedure.

A procedure, as discussed further herein, can be performed using or being assisted with image data. The image data can be image data acquired of a patient 28 using any appropriate imaging system, such as a MRI imaging system 26. The MRI imaging system 26 can be used to acquire both image data and diffusion data relating to the patient 28. The image data including diffusion data can also be reference to as gradient image data. The various types of data can be used to create images for viewing on the display 22. The image data can be used by a user or surgeon 25, such as during a navigated procedure. As discussed further herein, the various types of data, such as the diffusion data, can be used to illustrate tracts alone or tracts on image data acquired of the patient 28.

Image data acquired with the MRI imaging system 26 can use various algorithms to determine tracts based upon the acquired data. As discussed further herein, various tractography algorithms can require manual input, such as determination of a region of interest or a seed point, or can include automatic input. Further, multiple algorithms (e.g. linear, fast marching, energy, minimization, or other generally known algorithms) and multiple seed points can be used to define tracts relative to the image data of the patient 28. Therefore, various systems and methods can be used to determine confidence in a particular tract based upon the image data or multiple tractography methods.

The navigation system 20 can be used to navigate or track instruments including: catheters, probes, needles, guidewires, instruments, implants, deep brain stimulators, electrical leads, etc. The instrument 24 can be used in any region of the body. Also, any appropriate information about the instrument 24 can also be displayed on the display 22 for viewing by a surgeon 25.

Although the navigation system 20 can include an exemplary imaging device 26, one skilled in the art will understand that the discussion of the imaging device 26 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 26 that is used to acquire pre-, intra-, or post-operative or real-time image data of a patient 28. The illustrated imaging device 26 can be, for example, a magnetic resonance imaging device (MRI). Other imaging devices can include an x-ray C-arm having an x-ray source and an x-ray receiving section, computed tomography systems, etc. Any appropriate MRI system that can collect diffusion data can be used, as discussed herein. The imaging device 26 can be provided to acquire image data of the patient 28 prior to or during a procedure for diagnosis of the patient 28.

Although FIG. 1 illustrates an environmental view showing both the patient, surgeon, navigation system, and other elements, it will be understood that this is merely exemplary of all the portions that can be provided together. For example, an electromagnetic navigation or tracking system may not be provided in a room with the imaging MRI system 26, but is shown in FIG. 1 for illustration and can be separated for use in an actual procedure.

An imaging device controller 34 can control the imaging device 26 to capture and store the image data for later use. The controller 34 may also be separate from the imaging device 26. Also, the controller 34 can be used intra- or pre-operatively to control and obtain image data of the patient 28.

The image data can then be forwarded from the controller 34 to a processor system 40 via a communication system 41. The communication system 41 can be wireless, wired, a data transfer device (e.g. a CD-Rom or DVD-Rom), or any appropriate system. A work station 42 can include the processor system 40, the display 22, a user interface 44, and a memory 46. It will also be understood that the image data is not necessarily first retained in the controller 34, but may be directly transmitted to the workstation 42 or to a tracking system 50, as discussed herein.

The work station 42 provides facilities for displaying the image data as an image on the display 22, saving, digitally manipulating, or printing a hard copy image of the received image data. The user interface 44, which may be a keyboard, mouse, touch pen, touch screen or other suitable device, allows a physician or user to provide inputs to control the imaging device 26, via the controller 34, or adjust the display settings of the display 22.

The processor system 40 can process various types of data such as image data provided in the memory 46 or from the imaging system 26. The processor system 40 can also process navigation information, such as information provided from the tracking system 50. In addition, navigation processing can include determining a position of the tracked instruments relative to the patient 28 for display relative to the image data 23 on the display 22. The processor system 40 can also include a confidence system processor, as discussed further herein. It will be understood that each of the processing portions can be processed by separate or individual processors or can be processed substantially sequentially with an appropriate processor.

The optional imaging device 26 can be any appropriate 2D, 3D or 4D imaging modality. For example, an isocentric fluoroscopy, bi-plane fluoroscopy, O-ARM® imaging devices (i.e. devices sold by Medtronic Navigation, Inc. having a place of business in Massachusetts, USA), ultrasound, computed tomography (CT), T1 weighted magnetic resonance imaging (MRI), T2 weighted MRI, positron emission tomography (PET), optical coherence tomography (OCT), single photo emission computed tomography (SPECT), or planar gamma scintigraphy (PGS) may also be used.

The image data obtained of a patient can be used for various purposes. As discussed herein, image data can be obtained for performing a navigated procedure on an anatomy, planning an operation or procedure on an anatomy, and other appropriate reasons. For example, during a neurological procedure, it can be selected to obtain image data of a brain of the patient 28 for viewing during the procedure and navigating the instrument 24 relative to the image data 23. Further, the acquired image data can be used to plan the movement of the instrument 24 or for positioning of an implant during an operative procedure.

The imaging device 26 can also be used to obtain various types of data other than only image data. The various types of data can be used and overlaid one on another to obtain an appropriate image of the anatomy. For example, a magnetic resonance image can be obtained of a portion of the patient 28, such as a brain 29, for viewing in a selected manner. For example, a 3-D model can be formed of the brain based upon multiple slices of MRI data for displaying on the display 22 during a tracking of a navigated procedure.

The imaging device 26, if it is a MRI, can be used to acquire diffusion data of the patient 28. For example, diffusion data can be obtained relating to diffusion within the brain 29 or any other portion of the patient 28. For example, diffusion data relating to the brain 29 can be acquired and displayed in a graphical representation relative to the image data 23 on the display 22. The diffusion data can be illustrated in any appropriate manner and can be used to identify various structures, such as white matter tracts in the brain 29. Tractography methods and algorithms, including those discussed further herein, can be used to identify the white matter tracts within the brain 29. The determination of the white matter tracts can be based on algorithms that use diffusion data, such as a tensor determined from the diffusion data. As is understood by one skilled in the art, diffusion tensor image (DTI) data can be used to illustrate the various portions of the anatomy based upon an average or general diffusion within a voxel of the image data acquired by the imaging system 26. See The Visualization Handbook, "Diffusion Tensor MRI Visualization," pgs. 317-330 (2004) which is incorporated herein by reference.

During a magnetic resonance image acquisition of the brain 29, data is collected that can illustrate diffusion of water through the anatomy, such as with a tensor. The diffusion of water through the anatomy can be based upon various physical and anatomical constraints on the diffusion. Isotropic movement of water can occur within portions of the anatomy where water is substantially unconstrained by anatomical regions. For example, grey matter in the brain can allow for substantially isotropic diffusion of water. The movement of water in grey matter includes substantially only random movement and no constrained movement. A DTI of the grey matter would show the vector movement of the water to be substantially random from period to period in MRI data.

Anisotropic diffusion can occur in substantially constrained areas. For example, in the white matter in the anatomy diffusion of water can be substantially anisotropic. Anisotropic movement of water can allow or illustrate substantially constrained or connected areas within a selected portion of the anatomy. It will be understood that anisotropic movements of water can also occur in other areas, such as in veins, vessels, muscle fibers, nerve fibers and the lymph system. The anisotropic movement of the water is generally constrained by the walls of the fiber, such as neuron-fibers, and can be used to substantially map or track the fiber. Any matter, and not only water, can have anisotropic movement in any appropriate environment. Thus, discussion herein of anisotropic movement of water is merely exemplary. For example, a fiber tract can be defined by the movement of the water over a period of time within the fiber, the movement of water within the fiber can allow for tractography which can be used to illustrate or estimate a tract or path of the fiber. It will be understood that the discussion herein to a particular fiber, such as a neuron-fiber or white matter in the brain, can also relate to any appropriate fiber in the anatomy, including a vessel, endocrine movement vessel, or the like.

As discussed above, the vector of the movement of the water can be defined by an Eigenvector that is derived from a tensor matrix. The tensor matrix can define a vector of the movement of the water at a particular period in time. The Eigenvector or value generally relates to one voxel of image data and can be "connected" or "interrelated" to determine a tract. Various known algorithms, as further discussed herein, can then be executed by a user, a processor, or combinations thereof to illustrate a tract of a particular fiber.

Figure 2:
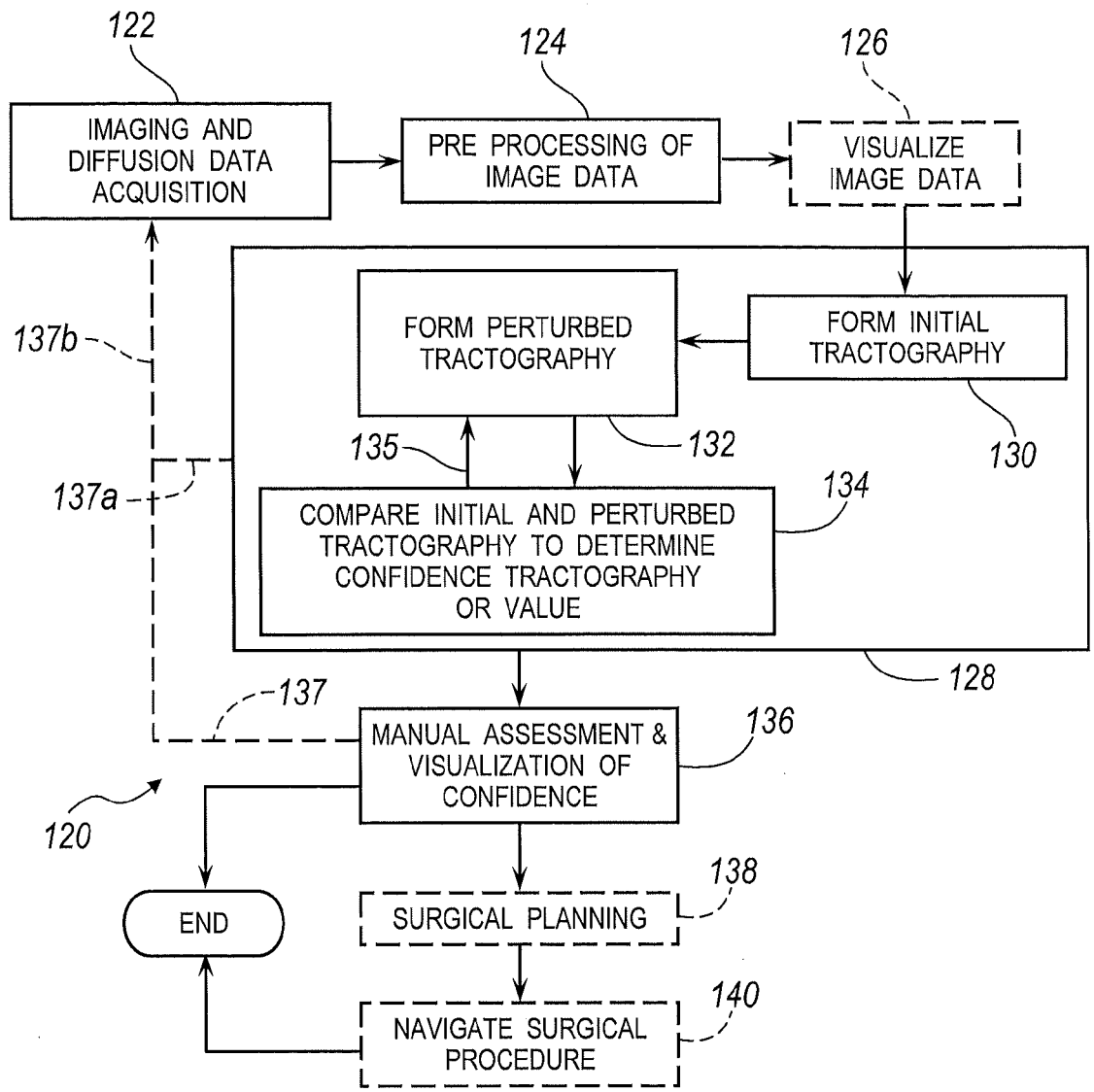
FIG. 2 is a flow chart illustrating the general steps of formulating or determining a confidence tractography.

With reference to FIG. 2, a visualization or tractography confidence system 120 is illustrated. The visualization system 120 can be understood to be an overview or a broad definition of a visualization system that can be used for determining a tract using DTI. The DTI data can be obtained with an appropriate system, such as the system illustrated in FIG. 1 and a procedure can also be tracked therewith. The confidence system 120 can include or be defined by algorithms to process data with the processor system 40. The tract can be any appropriate anatomical tract, such as a neurological tract, circulatory tract, muscular tract, or any appropriate tract system or combination of systems. Therefore, the visualization system 120 can be used for any appropriate anatomical system.

Initially, imaging is performed to acquire the image data and other data in block 122. It will be understood that the image data acquisition can be distinct from the data acquisition of the diffusion data or it can be substantially complimentary. For example, the image data can include T1 MRI or T2 MRI. The diffusion data acquisition can include the diffusion data of the water within the imaged area and can be acquired substantially simultaneously with the image data. The image data including data regarding movement of a matter, such as water, can also be referred to as gradient image data. The gradient image data is generally obtained as MRI data. The gradient image data includes information regarding a preferred or tendency direction of the flow of the matter within a specific region.

Pre-processing of the image data can be performed in block 124. Pre-processing of the image data can include smoothing the image data, refining the image data, storing the image data in an appropriate format, or the like. It will be understood that the pre-processing image data can include any processing that can be performed by an appropriate processor or system to prepare the image data and the diffusion data for the system 120. Further, the pre-processing of the image data can include overlying or superimposing the diffusion data on the image data.

Visualization of the data can be performed in block 126. It will be understood that visualization at this time can be optional and need not be required by the system 120. Nevertheless, the visualization of the pre-processed image data can include visualization of the broad diffusion data superimposed on an appropriate image data or visualization of the image data relative to the diffusion data for an initial analysis.

The acquired image data and diffusion can be entered into a confidence building or determining sub-routine (CBS) 128. The confidence building sub-routine 128 is illustrated and described here briefly, it will be described in more detail herein. Initially, the CBS 128 can provide for an initial tractography or first estimate in block 130. The initial tractography 130 can include any appropriate tractography method using the diffusion data. For example, the initial tractography can include a first portion such as an initial seed point, an initial algorithm, an initial data set, or the like. Nevertheless, the initial tractography performed in block 130 can then be subjected to a perturbation in a perturbed tractography block 132. The perturbed tractography or second estimate in block 132 can be based on any appropriate perturbation or change, such as a different seed point, region of interest (ROI), tractography algorithm, data set, initialization technique, or the like. As discussed herein, the perturbation can change the initial seed point, the initial algorithm, the initial data set to a second or different seed point, algorithm, or data set. A second tract or estimate can be formed based upon the change.

The perturbed tractography in block 132 can be compared to the initial tractography in block 130 to produce a confidence tractography in block 134. The confidence tractography in block 134 can be used to determine a confidence factor based on multiple tractography methods, multiple seed points, or any other appropriate system to produce a confidence tractography or value in block 134. The confidence tractography in block 134, as discussed further herein, can be used to insure an appropriate determination of tract, an identification of a selected anatomical feature, or the like. The confidence can also include a value or interval for any of the determined tracts.

The confidence information in block 134 can be determined based upon changes in a determined tract when a perturbation occurs. The confidence information can include sensitivity analysis and the like regarding the amount of change in a tract based upon a perturbation or whether a small perturbation results in a large tractography change. Thus, the confidence information can include sensitivity information or analysis. The sensitivity can also be reviewed, as discussed further herein, by a user.

The confidence tractography information from block 134 can be used to determine whether or not a further perturbation or change can be used or required to increase the confidence of the tractography. For example, an additional perturbation can occur by returning along path 135 to the perturbed tractography block 132. An additional change or perturbation can be chosen, and a tract regrown for comparison to the initial tractography from block 130 or to a previously formed perturbed tractography. Therefore, it will be understood that the iterative path 135 can be used, as discussed further herein, to provide a multiple perturbation or tractographies to assist in providing as high a confidence as possible in block 134.

It can be selected to obtain a certain confidence interval or factor in the tract that is determined in the confidence tractography in block 134. The confidence tractography in block 134 can be used to create a tractography that is within a selected trigger or confidence threshold. As discussed further herein, various techniques can be used to assist in attempting to obtain a confidence factor at a certain level in preparation for performing or planning a procedure. Regardless, the confidence tractography in block 134 can be provided as a substantially internal comparison when comparing the initial tractography and the perturbed tractography.

The confidence tractography in block 134 can then be visualized or analyzed by a user in block 136 as the confidence visualization. The confidence visualization in block 136 can include any appropriate information, such as a statistical confidence of the confidence tractography from block 134, a "confidence" or average tract determined in the confidence tractography in block 134, multiple tracts determined through the initial tractography and the perturbation of the tractography in blocks 130, 132 respectively, or any other appropriate information.

The confidence visualization in block 136 allows a user, such as the surgeon 25, to visualize the results of the confidence system 128. The confidence visualization block 136 can include visualizing multiple determined tracts, the confidence of any particular tract, or other appropriate information. Generally the confidence visualization in block 136 allows a user to analyze the data produced or the results determined by the system 128.

The analysis in block 136 can allow a user to input into the system or make a determination of confidence in the determined tractography as well. For example, a user can view the determined tractographies and the information related with each tract and apply the user's knowledge and experience in determining a confidence. For example, a low confidence may be given to a selected tract based upon the perturbation. The user, however, may know or understand that a small perturbation may lead to a large tract change due to a confluence of tracts in the area under study. Thus, the user may assign a high confidence to a determined tract. In other words, the system 120 can include both a system 128 confidence, a user confidence, and/or combinations of both.

In addition, a further iteration loop 137 can be provided from the confidence visualization block 136. The iteration loop 137 can include two paths. A first path 137a allows a user to require further iterations of the confidence system 128. This can assist in further analyzing the originally acquired image data to determine whether a greater confidence factor can be determined. A second feedback path 137b can allow the user to require the acquisition of further or different image data and diffusion data in block 122 to start the process completely over. This can be used if the image data that is acquired is not adequate, proper, or at a high enough resolution, or the like for achieving an appropriate confidence factor.

The image and diffusion data acquired in block 122 can be pre-operative data or diagnostic data. Therefore, it can be used to diagnose or examine the patient 28 at any appropriate time, such as long before a procedure. If a surgery is determined to be necessary, a surgical plan can be formed in block 138, based upon the confidence visualization in block 136. In addition, the surgical planning in block 138 can use the additional data, the confidence visualization, or any appropriate information to determine a surgical plan. The initial, perturbed, or confidence tractographies can be used to verify the location of various anatomical portions that are difficult to visualize or substantially indistinguishable from surrounding anatomical tissue. For example, various anatomical landmarks, such as an anterior commissure, posterior commissure, injured anatomical regions, or the like can be visualized relative to a tract formed in the tractography for determination of and performing the surgical procedure.

Finally, in block 140, a procedure can be performed, with or without navigation. The navigated procedure can be performed based upon the plan formed in block 138 and using the navigation system 20. Again, planning or performing a surgery is optional, but if one is performed tracts can be visualized and displayed on the appropriate display 22, as discussed herein, for use during a surgical procedure. Alternatively, the tractography information can be used only during the surgical planning 138 and only a display of the image data in a selected plan can be displayed. Nevertheless, the navigated procedure in block 140 can be based, at least in part, on the tract formed in the confidence tractography in block 134 and visualized with the confidence visualization in block 136.

Figure 3:
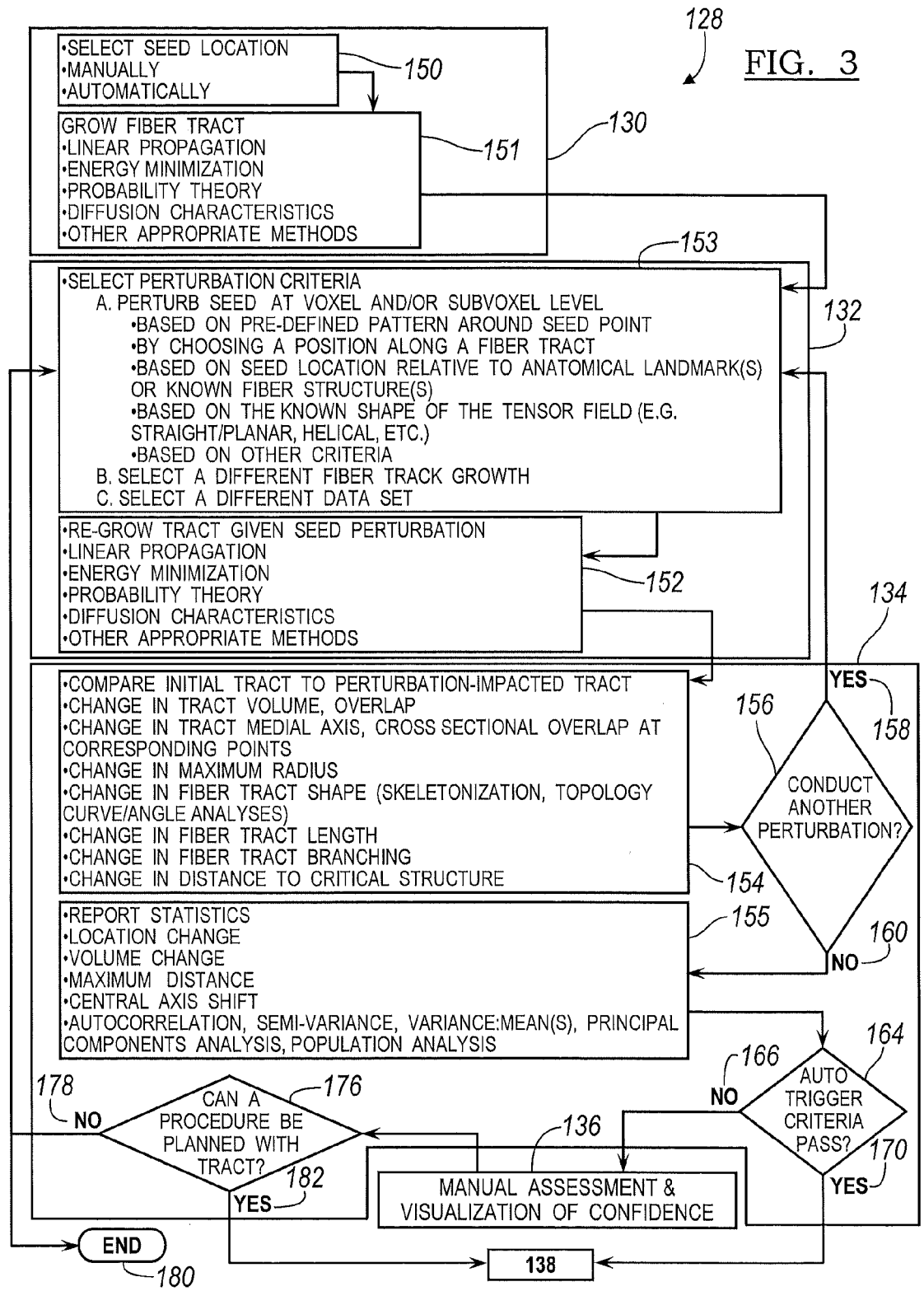
FIG. 3 is a detailed flow chart of a confidence building procedure in determining a tractography.

With reference to FIG. 3, the CBS 128 is illustrated in more detail. The CBS 128 can include various portions or procedures, as will be discussed further herein, to allow for a particular or selected confidence interval of a selected or determined anatomical tract. It will be further understood that the CBS 128 can be used to determine an appropriate confidence level or factor in a selected or prepared tractography. It will be understood, however, that selected data may not allow a particular confidence factor to be achieved. If a selected confidence factor can not be obtained, additional data can be obtained, no confidence tract may be produced, or any appropriate technique or procedure may be performed. Nevertheless, the CBS 128 can be used to at least determine a confidence factor or value for a selected tract or tractography method.

The initial tractography block 130 can include selecting an initial seed point in block or region of interest (ROI) 150 and determining or growing an initial tract in block 151. In block 150, of the CBS 128, an initial or first seed location can be determined or selected. It will be understood that a seed location can be determined in the image data or the diffusion data, obtained in block 122, in any appropriate manner. For example, the seed location can be determined substantially manually or automatically. Moreover, the seed point 150, as used herein, may also refer to a region of interest (ROI) including multiple seed points. A tract may be grown from each seed point within the ROI for analysis.

During manual seed location determination, a user can view the image data and determine a selected seed point. The seed point can include a seed pixel, a seed voxel, a seed sub-voxel, or any appropriate seed data point. The image data can also include raw diffusion data or any appropriate data to be viewed by a user. The seed point can be based upon the image data alone, the diffusion data, or combinations thereof. For example, the diffusion data can be used to assist the user in determining a selected region to use as a seed voxel or point.

In manual selection of a seed point, generally a local seed point or ROI is determined. The local seed point can be selected by a user using the image data in an area generally of interest to the user. The seed point can include a portion within grey matter, a portion within white matter, a portion within muscle tissue, or any other appropriate portion. Generally, the local region is the region of interest known to the user in which a tract is generally understood to have a beginning, end, or clear middle portion. The local region can include a generally well known region of the anatomy, such as a portion of the brain 29.

In addition or alternatively, an automatic determination of a seed point can be used to assist in selecting the appropriate seed point. For example, the image data can be used to determine a beginning portion of a tract or fiber, a middle portion, or any appropriate portion or region of the anatomy. The seed point can be determined based upon a selected algorithm or type of image data, such as bright region of the image data, a high contrast region of the image data, or any appropriate information. Further, a user's skill and knowledge can also be used to assist in determining a seed point in an automatic method such as selecting a region in which the seed point can be located. Regardless, the seed point automatically identified can be used by an appropriate algorithm, such as a tractography algorithm or method.

The seed points can be selected based upon the goals of the tractography assessment, such as determining a neuron-fiber tract, a muscle fiber tract or any other appropriate tract. Generally, automatic seed points can be based upon analysis of an entire region, such as an entire brain volume, to attempt to select a feature. In addition, seed points can be selected from a pre-selected grid volume or selected from within possible tracts within a region of interests. Further, seed points can be selected from regions of particular types of matter or data, such as high linear anisotropy. Nevertheless, one will understand that seed points can be selected from any appropriate region based upon any appropriate criteria. As discussed herein, the seed points can be perturbed or changed to assist in determining a confidence or error analysis of an initial tract.

Once the initial seed location or point has been determined in block 150, the initial tractography or growth of the tract can be performed in the block 151. Also the initial tract or tractography can be referred to and understood as a first estimate. As discussed herein, the initial tractography or the first estimate of an anatomical structure, can be refined or changed as discussed herein.

The initial growth of the tract in block 151 can be according to any appropriate method. For example, linear propagation, energy minimization, probability theory, diffusion characteristics, fast marching method, or any appropriate algorithm can be used to determine a tract. The various tractography algorithms can include those discussed above or those generally known in the art. For example, various tractography methods or algorithms are described in Mori et al. Fiber Tracking: principles and strategies, a technical review, NMR Biomed, Ch. 15, pp. 468-480 (2002), incorporated herein by reference. The various algorithms can be used to create an initial tract or first estimate based upon the initial seed point selected in block 150. The tract can be based upon the DTI of the diffusion data from the MRI and can be used to determine a tract based upon or beginning with the seed point. The tract can be a neurological tract, a vascular tract, a muscle tract, or the like. Further, the various tractography methods or algorithms can be selected based upon certain information or considerations, such as time constraints, branching information, or the like. It will be understood that the initial tract formed in the initial tractography block 130 can be one defined by a single one or multiple tractography algorithms or techniques. Therefore, the initial tractography can include a single or multiple initial tracts that are based upon one or more algorithm or tractography methods.

Once the initial tractography has been performed in block 130, the perturbation of the tractography or a perturbation of a portion of the tract can be performed in block 132. The perturbation can also include perturbing the seed point in block 153 and regrowing or forming a second estimate in block 152. The perturbation of the tractography can include any appropriate perturbation. For example, a seed point perturbation can be performed. In other words, a change in the seed point can be made from the initial seed point in block 150. The perturbed or changed seed point is selected in block 153. The seed point can be changed at a level of a pixel, voxel or sub-voxel. Also, the ROI can be moved to include a plurality of seed points. Some of the perturbed ROI can overlap the initial ROI, but tracts can be grown from each point in the perturbed ROI as well. For example, at the sub-voxel level, only a portion of the voxel may be used as a seed point. Therefore, a different selected region of the seed voxel can be used as the seed or the starting point for the tractography.

The seed voxel perturbation can be based upon various information. For example, a predefined perturbation or selection pattern can be selected, based upon the initial seed voxel determined in block 150. The predefined perturbation pattern can include any appropriate pattern, such as a geometrical shape, a distance, a contrast, or the like. The predefined perturbation pattern can be included in the memory system 46 and executed by the processor system 40 for a substantially automatic perturbation technique.

For example, the initial seed voxel can be selected based upon any appropriate technique, including those discussed above. The perturbed or different selected seed voxel can be selected as being within a predefined region or geometry based upon the first seed voxel. For example, the second or perturbed seed voxel can be selected to be touching the first seed voxel or within a particular number of voxels of the first or initial seed voxel. Therefore, the perturbation of the seed voxel can be based upon any appropriate selection or perturbation technique, such as defining an area around the initial seed voxel.

A further perturbation criteria from block 153 can include determining or selecting a position along the tract defined in the initial tractography in block 130. The position defined along the tract can then be used as a seed voxel or seed point to define the tract from that point forward and may also backtrack along the defined tract to insure that the tractography to reach the selected point was appropriate. The point selected along the tract defined in the initial tractography from block 130 can be one that is automatically selected by the processor 40 or program or can be selected by a user. For example, instructions can be executed to select a point that is a distance from the initial seed point along the tract defined at the initial tractography in block 130. Alternatively, or in addition to the automatic location definition, a user can define a point or select a point within a tract for the perturbed or second seed point. The user can use the initial visualization or a pre-confidence visualization to select the location along the tract for the perturbation technique. For example, a user can select a point near a determined branch or where a user may theorize a branch to be to assist in the perturbation or confidence of the tract from the initial tractography in block 130.

A further perturbation technique can include selecting a different seed location based upon a known anatomical landmark, a known fiber structure, a known anatomical disturbance, or the like. For example, in the brain, various anatomical locations can be known, based upon image data thereof. One example can include an anterior commissure, a ventricle, a posterior commissure, or the like to be used as a different or second seed location. The tractography can then perturb the seed location based upon a known anatomical landmark to form a second or perturbed tractography. Further, a tract structure, fiber structure can be generally known by a user, by a program, or by combinations thereof to assist in determining the perturbed seed locations.

Because the diffusion data can be to determine tensor fields, the perturbed location can be based upon the tensor field types that are known. The tensor field types can be based upon the type of diffusion occurring within the anatomy and that information can be used to determine the perturbed seed location. Although various perturbation techniques are described above, one skilled in the art will understand that any appropriate perturbation technique can be used to determine or select a second or multiple different seed locations.

Once a perturbed seed location has been determined in block 153, the tractography can be again performed to form the second estimate in block 152. The tractography in block 152 can include any appropriate tractography algorithm that can be the same or different than the algorithm from the initial tractography in block 130. Also the second tractography in block 152 can be understood to be a second estimate of the tract or anatomical structure. The second estimate based on the perturbed seed point or any perturbed criteria can be compared to the first estimate, or discussed herein. It will be understood, however, that any appropriate number of estimates can be performed. Thus the second estimate can also include a third, fourth, etc. Thus the perturbed tractography in block 132 can include an internal iteration to form any appropriate number of perturbed tractographies.

It will be understood that the same tractography algorithm can be used with the new seed location and be directly compared to the algorithm results from block 130. Further, different tractography algorithms can be used and the tracts defined by the different algorithms can then be compared to the initial tractography from block 130. As discussed above, the use of multiple tractography algorithms can be used as a part of the perturbation in block 132.

Once the tract has been regrown in block 152, a comparison of the initial tract from block 130 and the perturbation tractography from block 132 can be performed in the confidence tractography block 134. The confidence tractography 134 can include various portions and decision blocks including the initial comparison or information gathering in block 154, the reporting block 155, and decision blocks regarding whether to conduct another perturbation in block 156, determining whether a trigger has been passed, and determining whether a procedure can be planned based upon the tract in block 176.

Therefore, the comparison and confidence tractography in block 134 can include various portions as discussed further herein. The comparison information can include any appropriate information, such as: tract volume change, tract overlap change, tract medial axis change, tract cross-sectional overlap at various corresponding points change, tract maximum radius change, tract fiber shape change (skeletonization topology, curve/angle analysis), change in tract length, change in tract branching, change in distance to critical or selected structures, or any other appropriate indicators. The comparison of various information can be used to determine a difference between the initial tractography (i.e. first estimate) from block 130 and the perturbed tractography (i.e. second estimate) from block 132. It will be understood that any appropriate changes can be compared between the various tracts and those discussed herein are merely exemplary.

Once the comparison has been performed in block 154, a determination of whether another perturbation should be performed can be a in block 156. The determination of whether another perturbation should be performed in block 156 can be based on various indications or selection criterion. For example, a minimum number of perturbations can be performed for comparison in block 154. Further, an initial level of difference in comparison can be selected and, if this is exceeded a further perturbation may occur. It will be understood by those skilled in the art that any appropriate criteria can be selected for determining whether additional perturbation should occur in block 156. If the determination is YES 158 in decision block 156, then the system can iterate back to the perturbation tractography block 132. A new seed location or any appropriate information can then be input into the system in block 132 and the tract can be regrown in block 152 and then compared to the initial, the second, or any previous grown tract in block 154.

If the determination to conduct additional perturbation is NO 160 in decision block 156, then the information can be forwarded to the confidence block 155. The statistics report in the confidence block 155 can include any appropriate information and can be displayed or output to a user in any appropriate manner. For example, the statistics or information can include location changes, volume changes, maximum distance changes, central axis shift, auto correlation, semi-variance, variance of the mean, principle component analysis, population analysis, various particular information, such as the particular comparisons in block 154 or any appropriate information. Therefore, the confidence tractography in block 155 can be used to determine the confidence of a particular tract that includes a single one or a combination of multiple tracts, based upon the perturbation in block 155 and the comparison block 154.

The statistics reported in block 155 can be used by a user or the confidence system 120 to assist in determining the confidence or other analysis of the initial tract, the regrown tract or second estimate, or the like, For example, as illustrated further herein, the reported statistics can include the difference between the first estimates and the second estimate of the tract. The statistics therefore, can be used to determine the confidence in a particular tract based upon the image data. Further, the difference between the first estimate and the second estimate can be used for further analysis if selected.

The statistics in block 155 can be output for comparison to an auto trigger pass in decision block 164. The auto trigger pass in decision block 164 can be any appropriate trigger, such as determining whether a selected confidence interval, factor, value, of threshold has been achieved or not. The trigger can be any appropriate pre-selected trigger such as the appropriate confidence interval, factor, value, or threshold. The trigger can include an appropriate value for any of the selected or determined statistics. For example, a maximum location change between the first estimate and the second estimate can be used for the trigger criteria. If the first estimate and the second estimate are within a maximum location change value, then the trigger criteria can be determined to have been passed. One skilled in the art, however, will understand that any appropriate trigger criteria can be selected.

If the selected trigger criteria have not been achieved or if such determination is NO 166 in block 164, a manual assessment can be performed in block 168. The manual assessment in block 168 can include a visualization of the confidence visualization, as discussed above in block 136. The manual or visual assessment in block 168 can be used by a user, such as the surgeon 25, to determine whether the DTI data or the tracts formed therefrom are appropriate or should be retained for a particular patient. The manual assessment can use the criteria from the auto trigger criteria decision block 164 except that a determination can be made by a user rather than a processor system. In addition, the user can use other criteria to determine whether the formed tracts are appropriate. For example, the user can use the user's experience to determine whether the data is appropriate for use.

If the auto trigger criteria pass in block 164 is determined to be NO 166, the manual assessment and visualization can occur in block 168. After or concurrent with the manual assessment and visualization in block 168, a determination can be made as to whether the procedure can proceed or whether a procedure can be planned with the tract information, which can also include the confidence information, in decision block 176. The determination of whether the procedure can occur after the manual assessment and visualization can be substantially automatic, such as with the assistance of a processor, or substantially manual.

If the determination is YES 182 from the procedure planning determination block 176, then the confidence information can be visualized in block 136, or the procedure can be planned in block 138 just as if the auto trigger criteria pass had been YES 170 in decision block 164. Therefore, the manual assessment and visualization block 168 can lead to the determination block 176 to determine whether the procedure can occur even if the auto trigger criteria pass in block 164 is determined to be NO 166.

Alternatively, if the determination of whether the procedure can proceed in block 176 is NO 178 then the procedure can iterate back to block 132 to grow a tract according to any appropriate procedure, algorithm, or method. Therefore, if the assessment determines that the confidence factor is not great enough or the tract is not appropriate, then the procedure can be re-iterated through block 132. Further, if the manual assessment and visualization is determined to be too different or the confidence factor is not within a predetermined level the procedure can end in block 180. If the procedure ends in block 180, different image data can be acquired, if selected, or a procedure can proceed without the tractography information. In this case, the procedure can proceed based upon a user's, such as the surgeon's 25, prior knowledge, skill, or the like with assistance of various other devices if so selected. Nevertheless, the determination of whether the procedure can occur based upon the confidence factor can, in certain instances, be NO 178 and the END block 180 can be reached.

If the auto trigger pass is determined to be a YES 170, then the procedure can proceed to the confidence visualization in block 136, with an appropriate confidence and error analysis information provided to a user, and a procedure can be planned in block 138. As discussed above, the confidence and tractography information provided to the user can be any appropriate confidence information or can simply be a visualization that meets a predetermined or preselected confidence interval. Therefore, the confidence visualization in block 136 can be used for both a manual assessment when a confidence interval has not (e.g. NO path 166) been achieved or for visualization of the tractography that achieves an appropriate confidence interval. One skilled in the art will understand that the tract and confidence factor information can be determined pre-operatively or intra-operatively. Thus the system 120 can be substantially a planning system, a navigation system, or combinations thereof. The confidence visualization in block 136 can also be used by a user to determine manually whether further data should be obtained or further perturbations should occur.

As discussed above, various techniques and algorithms can be used in a tractography method. The various algorithms use different techniques for analyzing and determining the data for creating or determining a tract. It can be selected to use multiple techniques to achieve a confidence interval for a selected tract based upon the multiple techniques. Therefore, one skilled in the art will understand that the perturbation techniques or location confirming techniques can be used to enhance a sensitivity or tractography method to assist in enhancing the confidence in a particular tract.

The determination or estimate of an anatomical structure, as discussed above, can be used to assist in navigating a procedure relative to the patient 28. The determined tract structure and selected information can be displayed on the display 22 with an icon representing a position of the instrument 24 relative to the patient 28. Returning reference to FIG. 1, the navigation system 20 can further include the tracking system 50 that includes one or more localizers 52 (e.g. a coil array or multiple coil arrays), a coil array controller 54, a navigation interface 56 for an instrument tracking device, and a dynamic reference frame 58.

The dynamic reference frame 58 can include a dynamic reference frame member or holder 60 and a removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including a localizer. A tracking device 67 can also be associated with the instrument to track the instrument 24.

In an electromagnetic tracking system, the transmitter coil array 52 is controlled or driven by the coil array controller 54. Upon driving the coils in the transmitter coil array 52 with the coil array controller 54, electromagnetic fields are generated within the patient 28 in the area where the medical procedure is being performed, which is again sometimes referred to as patient space. The electromagnetic fields generated in the patient space induce currents in the tracking devices 62, 94 positioned on or in the instruments 24. These induced signals from the instrument 24 are delivered to the navigation device interface 56 and can be forwarded to the coil array controller 54. One skilled in the art will understand other details of an EM tracking system which are not discussed in further detail here. Various electromagnetic tracking systems are generally described in U.S. Pat. No. 5,913,820, entitled "Position Location System," issued Jun. 22, 1999; U.S. Pat. No. 5,592,939, entitled "Method and System for Navigating a Catheter Probe," issued Jan. 14, 1997; and U.S. Patent Application No. 2007/0249911, published Oct. 25, 2007, entitled "Method and Apparatus for Optimizing a Therapy", all of which are hereby incorporated by reference. The tracking system 50 may be a hybrid system that includes components from various tracking systems such as optical, acoustic, radiation, radar, etc. Communications within the system can include a wireless communications channel, such as that disclosed in U.S. Pat. No. 6,474,341, entitled "Surgical Communication Power System," issued Nov. 5, 2002, herein incorporated by reference, may be used.

Although the discussion above is directed to an electromagnetic navigation and tracking system, it will be understood that any appropriate tracking system can be used as the tracking system 50. For example, one skilled in the art will understand that an optical tracking system can be used, a radar tracking system can be used, an acoustic tracking system can be used, an accelerometer tracking system can be used, or any appropriate tracking system. Nevertheless, the tracking system can include any appropriate portions such as an appropriate localizer for the tracking system and appropriate tracking devices for the tracking system. Thus, the discussion herein regarding an electromagnetic tracking system is merely exemplary of any appropriate tracking system.

Briefly, the navigation system 20 operates as follows. The navigation system 20 creates a translation map between all points in the image data or image space and the corresponding points in the patient's anatomy in patient space (either manually or automatically, an exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.) The points selected can be fiducial marks 69 that include anatomical landmarks or artificial landmarks, such as those disclosed in U.S. Pat. No. 6,381,485, entitled "Registration of Human Anatomy Integrated for Electromagnetic Localization," issued Apr. 30, 2002, herein incorporated by reference. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the controller 34 identify the corresponding point on the pre-acquired image or atlas model relative to the tracked instrument 24 and display the position on display 22 and relative to the image data 23. This identification is known as navigation or localization. An icon representing the localized point or instruments is shown on the display 22 within several two-dimensional image planes, as well as on three and four dimensional images and models. In order to maintain registration accuracy, the navigation system 20 can continuously track the position of the patient 28 with the dynamic reference frame 58.

The instrument 24 used in a procedure can be any appropriate instrument (e.g., a catheter, a probe, a guide, etc.) and can be used for various procedures and methods, such as delivering a material or providing electrical stimulation to a selected portion of the patient 28, such as within the brain 29. The material can be any appropriate material such as a bio-active material, a pharmacological material, a contrast agent, or any appropriate material. As discussed further herein, the instrument 24 can be precisely positioned via the navigation system 20 and otherwise used to achieve a protocol for positioning the material relative to the patient 28 in any appropriate manner, such as within the brain 29. The instrument 24 may also include a brain probe to perform deep brain stimulation.

The confidence tractography system 120, including the detailed CBS 128, can be carried out or performed with the navigation system 20, or portions thereof. As discussed above, the processor system 40 can include a processor that is operable to execute the error analysis or confidence system 120. As discussed above, image data can be obtained with the MRI imaging system 26 and can be processed with the processing system 40 for performing or preparing a surgical plan.

With exemplary reference to a neurological procedure within a brain/cranium 29 of the patient 28, the confidence system 120 can use image data of the patient 28 to assist in determining an appropriate tract of a selected portion of the anatomy. The tract can be determined in a brain 29 that is within the image data 23 and displayed on the display 22. The display 22 can be provided with the workstation 42 or provided as a separate system. It will be understood, therefore, that the processing and the confidence system 120 can be performed at any appropriate location and at any appropriate time such as pre-operatively, intra-operatively, or post-operatively.

Figure 4:
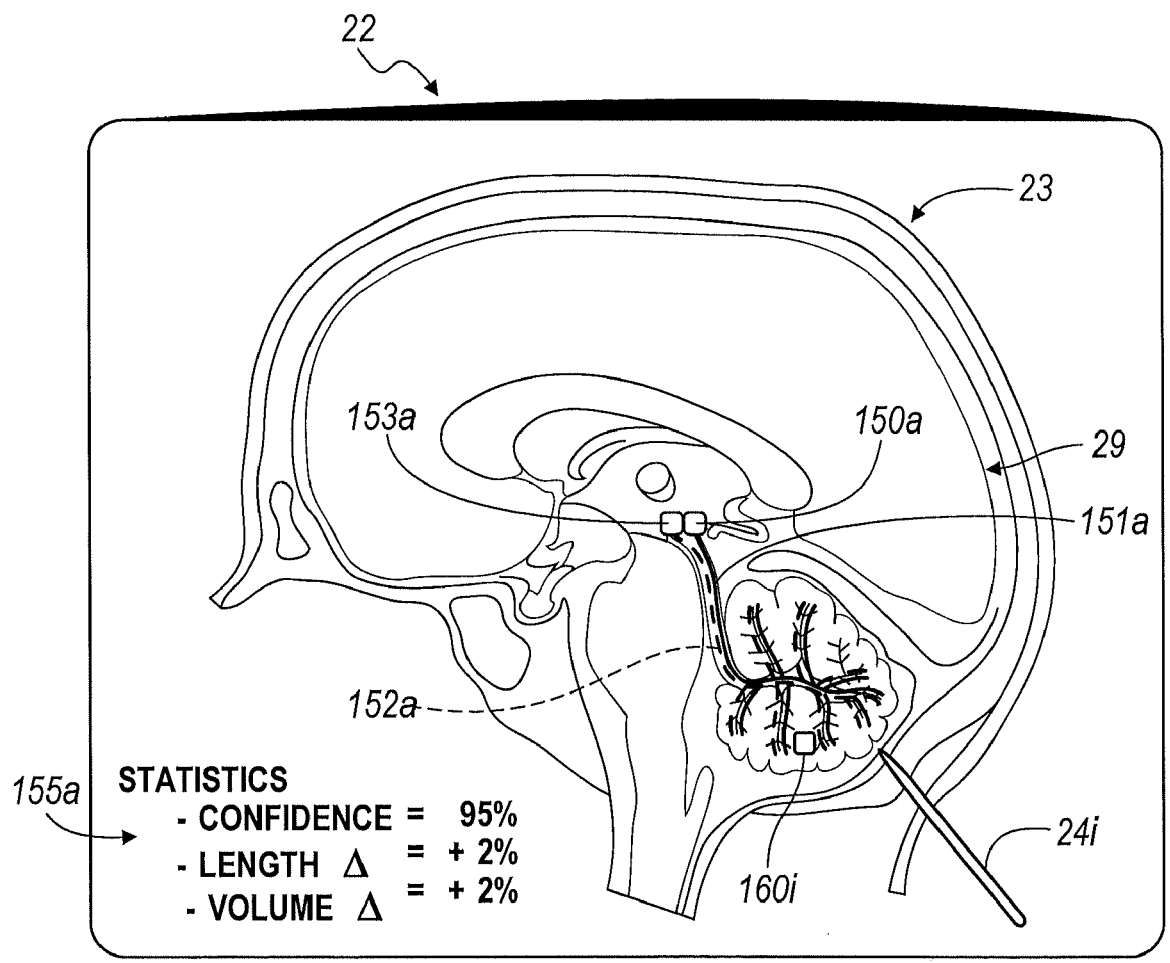
FIG. 4 graphically illustrates a visualization of a confidence tractography system according to various embodiments.

With reference to FIGS. 2-3 and 4, the confidence system 120 can be used to assist in determining the confidence in a particular tract identified within the image data 23 based upon various types of data, such as diffusion data. The image data can be obtained in block 122 and pre-processed in block 124. The data can then be processed in the CBS 128 to assist in determining a tract and providing a confidence or error analysis of the tract or various tracts.

With reference to FIG. 4, the initial seed location from block 150 can be selected as 150a. It will be understood that the initial seed location 150a can be any appropriate seed location, it can be determined in any appropriate manner, such as manually or automatically or combinations thereof as discussed above. An initial fiber tract or first estimate 151a can then be formed based upon the image data and illustrated as a line or group of lines on the image data. The initial fiber tract 151a can be determined in any appropriate manner, including those discussed above. Further, both the initial seed location 150a and the initial fiber tract 151a can be displayed relative to the image data 23 of the patient 28. For example, the seed location 150a and the tract 151a can be superimposed as an icon representing the initial seed location 150a and the initial tract 151a on the image data 23 on the display 22. Nevertheless, it will also be understood that the processing system 40 can prepare the various tracts substantially in memory and only display various portions, such as the statistics in block 155 or an image for the manual assessment in block 136. Therefore, the illustration of the initial seed location 150a, the initial tractography 151a, and other portions is merely exemplary for discussion of this example.

The perturbed or changed seed location 153a can then be selected and a tract can be regrown to produce a perturbed tract or second estimate 152a. At this point, it can be determined in block 156 whether additional perturbation is required. As discussed above, the confidence system 120 can include a preselected number of perturbations and one, two, or more can be provided such that only a first or initial seed location and a single perturbed seed location is not necessary, but discussed herein merely for efficiency and clarity of the current discussion.

After the first or initial tract 151*a* has been created or determined and the second tract 152*a* has been determined, the two tracts can be compared in block 154. Again, it will be understood by one skilled in the art that the two tracts 151*a* and 152*a* can be illustrated on the display 22 or can be provided in the memory 46, or combinations thereof, and displaying them on the display 22 is merely exemplary. Nevertheless, the two tracts 151*a*, 152*a* can be overlaid on image data 23 for visualization by a selected user.

Once the comparison in block 154 has been performed, the statistics in block 155 can be determined and recorded. The statistics can include any appropriate statistics, such as a confidence factor, a length differential change, a volume differential, or any appropriate statistics. Again, the statistics 155*a* can be recorded and displayed on the display 22 for viewing by the user 25 or can be stored in the memory 46 for determining whether the auto trigger criteria has been passed in block 164.

Based upon the information determined, including the displayed statistics 155*a*, an appropriate procedure can then be determined to be performed on the patient 28 with assistance with of the tractography. For example, the various types of data can be displayed on the display 22, including the image data of the brain 29 and the various tracts 151*a*, 152*a*. It will be understood that a selected tract may be displayed on the image data 23 while performing of a procedure, such as the first estimate, the second estimate, an average thereof, a boundary defined by the estimates, or any combination thereof.

As discussed above, a procedure can be planned with the assistance of the tractography and the confidence in the selected or appropriate tract. This can allow for guiding a selected instrument, such as a deep brain stimulation probe, relative to a selected region. The probe can be the instrument 24 which can be represented on the display 22 as an icon 24*i*. Further the display 22 can include a target location icon 160*i* to assist the user 25 in determining whether the instrument 24 has reached an appropriate location.

Therefore, the tractography data can be used by the user 25 to assist in determining an appropriate location for a treatment or identification of a selected anatomical structure or portion. This can assist the user 25 in performing the procedure on the patient and determining an appropriate location for the instrument 24. The navigation system 20 can be used to navigate the instrument relative to the patient 28 in any appropriate manner, including those discussed above, to determine whether the instrument 24 has reached a selected location and can be displayed on the display 22.

The tractography can be used to assist in identifying various regions of the anatomy, such as muscle fiber tracts in the heart or neural fiber tracts in the brain and spinal chord. The above description relating to a procedure in the brain 29 is merely exemplary. One skilled in the art will understand that diffusion data can be acquired for any appropriate portion of the anatomy, such as a spinal column, to define fiber tracts therein. Thus, DTI can be used to determine the location and structure of fiber tracts in the spinal column for various purposes, such as a surgical procedure, analysis, diagnosis, etc. Accordingly, one skilled in the art will understand that the procedures and systems discussed above are not limited to a procedure only within a brain, but can be related to any appropriate structure.

The confidence system 120 used in any appropriate procedure, including determining multiple tracts with perturbed parameters (e.g. seed points, algorithms, etc.), can be used by the surgeon 25 to ascertain a confidence in any determined tract. This can assist in diagnosis, study, or treating the patient 28 by providing a selected amount of confidence in an identified tract of the patient 28. Thus, the user 25 can be aware of the amount of confidence is present in the displayed or determined tract. This can also assist the user 25 in whether to rely on the tractography to perform or assist in performing a selected procedure.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method to determine a confidence in a displayed image data of an anatomy, comprising:
    obtaining image data of the anatomy including data regarding diffusion of a matter;
    executing a first instruction by a processor to determine a first seed portion and making a first estimate of an anatomical structure based upon the obtained image data by executing instructions with the processor to determine a first connection of multiple portions of the image data beginning with the first seed portion;
    executing a second instruction by the processor to determine a second seed portion and making a second estimate of the anatomical structure based upon the obtained image data by executing instructions to determine a second connection of multiple portions of the image data beginning with the second seed portion; wherein the second seed portion is different from the first seed portion for the first estimate, wherein the second seed portion is along a tract of the first estimate; and
    comparing the first estimate of the anatomical structure and the second estimate of the anatomical structure.

2. The method of claim 1, wherein the image data of the anatomy including data regarding diffusion of the matter includes:
    obtaining at least six magnetic resonance gradient images of the anatomy; and
    formulating a tensor defining the direction of diffusion of the matter within the anatomy.

3. The method of claim 1, wherein determining a second seed portion includes automatically selecting the second seed portion by executing an instruction with the processor.

4. The method of claim 3, wherein executing the second instruction includes selecting a portion in the image data a predetermined distance from the first seed portion, selecting an image portion within the first estimate, selecting an image portion a predetermined distance from the first estimate, or combinations thereof.

5. The method of claim 1, wherein comparing the first estimate of the anatomical structure and the second estimate of the anatomical structure includes determining a confidence factor of the second estimate of the anatomical structure, the first estimate of the anatomical structure, or combinations thereof.

6. The method of claim 5, wherein the confidence factor includes a change in the estimated anatomical structure location, a volume change of the estimated anatomical structure, a central axis shift of the anatomical structure, or combinations thereof.

7. The method of claim 5, wherein comparing the first estimate of the anatomical structure and the second estimate of the anatomical structure includes:
providing the processor, executing an instruction with the processor to determine a difference between the first estimate of the anatomical structure and the second estimate of the anatomical structure.

8. The method of claim 1, further comprising:
displaying information relating to the comparison of the first estimate of the anatomical structure and the second estimate of the anatomical structure.

9. The method of claim 8, further comprising:
determining whether a third estimate of the anatomical structure is required; and
performing a third estimate of the anatomical structure if it is determined that the third estimate is required.

10. The method of claim 9, further comprising:
comparing the third estimate of the anatomical structure to at least one of the first estimate of the anatomical structure, the second estimate of the anatomical structure, or combinations thereof.

11. The method of claim 1, further comprising:
navigating a procedure relative to at least one of the first estimate of the anatomical structure, the second estimate of the anatomical structure, or average of the first estimate and the second estimate, an area bounded by the first estimate and the second estimate, or combinations thereof.

12. The method of claim 11, further comprising:
providing a localization system;
providing a tracking device;
providing an instrument;
associating the tracking device with the instrument; and
tracking the tracking device with the localization system relative to at least the anatomy based upon at least one of the first estimates of the anatomical structure, the second estimate of the anatomical structure, or combinations thereof.

13. The method of claim 1 further comprising:
identifying the anatomical structure.

14. The method of claim 1 further comprising:
selecting the anatomical structure; and
wherein selecting the anatomical structure includes selecting at least one of a neurological region, a muscle fiber region, a circulatory region, or combinations thereof.

15. The method of claim 14, wherein the neurological region includes a fiber tract in the brain, a fiber tract in the spinal column, or combinations thereof.

16. A method of determining a confidence in a displayed image data of an anatomy, comprising:
determining a direction of diffusion of matter within the anatomy with an obtained gradient image data including formulating a tensor of the diffusion;
determining a first estimate of an anatomical structure based on at least one of selecting a first starting portion in the obtained image data or selecting a first tractography algorithm;
determining a second estimate of the anatomical structure based on at selecting a second starting portion in the obtained image data, wherein the second starting portion is along a tract of the first estimate; and
comparing the determined second estimate of the anatomical structure to the determined first estimate of the anatomical structure and determining a confidence value of the determined first estimate, second estimate, or combinations thereof of the anatomic structure;
wherein comparing the determined second estimate of the anatomical structure to the determined first estimate of the anatomical structure includes at least one of comparing a change in tract volume, a change in tract overlap, a change in tract medial axis position, a change in tract cross sectional overlap at corresponding points, a change in tract maximum radius, a change in tract distance to critical structures, or combinations thereof.

17. The method of claim 16, further comprising:
determining a third estimate of the anatomical structure;
determining a confidence value for each of the first estimate, the second estimate, and the third estimate; and
displaying on a display the determined confidence value for at least one of the first estimate, the second estimate, and the third estimate.

18. The method of claim 17, wherein displaying includes:
displaying a substantially anatomically correct representation of the anatomical structure.

19. The method of claim 16, further comprising:
displaying a representation of the determined confidence of the first estimate of the anatomical structure;
wherein determining the confidence of the first estimate of the anatomical structure includes comparing the first estimate to the second estimate of the anatomical structure.

20. The method of claim 16, wherein determining a direction of diffusion of the matter includes determining a vector substantially defining the movement of the matter through the anatomy based upon the gradients of the anatomy.

21. The method of claim 16 where selecting a first starting portion includes selecting at least one of a seed pixel, a seed voxel, a seed sub-voxel, a region of interest including a plurality of seed points, or combinations thereof.

22. The method of claim 16 wherein selecting a second starting portion includes at least one of selecting a seed pixel, selecting a seed voxel, selecting a seed sub-voxel, a region of interest including a plurality of seed points, or combinations thereof.

23. The method of claim 16, wherein determining the second estimate of the anatomical structure further includes selecting a second tractography algorithm;
wherein selecting the second tractography algorithm is selecting the second tractography algorithm to be different than the first tractography algorithm.

24. The method of claim 16 wherein determining the confidence of the determined first estimate of the anatomical structure includes comparing the first estimate of the anatomical structure to the determined second estimate of the anatomical structure.

25. The method of claim 24, wherein determining the confidence of the determined first estimate of the anatomical structure includes determining a difference between the determined second estimate of the anatomical structure and the determined first estimate of the anatomical structure.

26. The method of claim 25, wherein the difference between the second estimate of the anatomical structure and the determined first estimate of the anatomical structure includes at least one of a location change, a volume change, a maximum distance change, a central axis shift, a population analysis, a variance of means, a principal component analysis, or combinations thereof.

27. The method of claim 25, wherein the determined confidence of the determined first estimate of the anatomical structure increases as the difference between the determined second estimate of the anatomical structure and the determined first estimate of the anatomical structure lowers.

28. A method of claim 16, further comprising:
providing to a user the determined confidence of the first estimate of the anatomical structure.

29. The method of claim 16, further comprising:
determining whether the determined confidence of the determined first estimate of the anatomical structure passes a trigger criterion.

30. The method of claim 29, further comprising:
performing a procedure relative to the anatomy based upon the determined first estimate of the anatomical structure if the trigger criterion is passed.

31. The method of claim 16 further comprising:
selecting the anatomical structure.

32. The method of claim 31 wherein selecting the anatomical structure includes selecting a region of interest in at least one of the brain, the spinal column, the cardiovascular system, the muscular system, or combinations thereof.

33. The method of claim 17, further comprising:
displaying for a user each of the confidence of the first estimate, the confidence of the second estimate, and the confidence of the third estimate.

34. The method of claim 33, further comprising:
performing a procedure relative to the anatomy with a navigation system;
displaying the image data of the anatomy and displaying an icon representing an instrument relative to the image data;
defining a target based upon at least one of the first estimate of the anatomical structure; the second estimate of the anatomical structure; the third estimate of the anatomical structure; an average of the first estimate of the anatomical structure, the second estimate of the anatomical structure, and the third estimate of the anatomical structure; an area bounded by at least two of the first estimate of the anatomical structure, the second estimate of the anatomical structure, or the third estimate of the anatomical structure; or combinations thereof; and
navigating the instrument to the target.

35. The method of claim 16, wherein determining the second estimate of the anatomical structure based on selecting a second starting portion in the obtained image data includes automatically selecting the second starting portion.

36. A method of determining a confidence in a displayed image data of an anatomy, comprising:
determining a first estimate of an anatomical structure based at least in part on a formulated tensor of diffusion of a matter in an obtained gradient image data of the anatomy and a selected first criterion;
determining a second estimate of the anatomical structure based at least in part on a selected second criterion for the formulated tensor of diffusion of the matter in the obtained gradient image data of the anatomy, wherein selected second criterion is a second seed point different from a first seed point for the first estimate, wherein the second seed point is along a tract of the first estimate;
comparing the first estimate of the anatomical structure and the second estimate of the anatomical structure;
determining a difference between the first estimate of the anatomical structure and the second estimate of the anatomical structure;
determining a configuration of the anatomical structure; and
determining a confidence in the determined configuration of the anatomical structure based at least in part on the determined difference between the first estimate of the anatomical structure and the second estimate of the anatomical structure;
wherein the selected first criterion includes at least one of a seed portion, a tractography algorithm, a data set, or combinations thereof and the selected second criterion is different from the selected first criterion.

37. The method of claim 36, wherein the second criterion is selected automatically.

38. The method of claim 36, further comprising:
displaying a representation of the determined configuration of the anatomical structure, displaying the determined confidence of the determined configuration of the anatomical structure, determining whether the confidence of the determined configuration passes a trigger.

39. The method of claim 38, further comprising:
performing a procedure on the anatomy based upon the determined configuration of the anatomical structure if the determined confidence passes the trigger.

40. The method of claim 36 wherein determining a first estimate of the anatomical structure, determining the second estimate of the anatomical structure, or combinations thereof includes performing a tractography based upon the determined diffusion of the matter.

41. The method of claim 36, wherein determining the configuration of the anatomical structure includes illustrating a neurological fiber tract, a muscle fiber tract, a vessel tract, or combinations thereof.

42. The method of claim 36, further comprising:
providing a navigation system;
associating a tracking device with an instrument; and
navigating the instrument relative to the anatomy based upon the determined configuration of the anatomical structure.

43. The method of claim 42, further comprising:
providing a display;
displaying the determined configuration of the anatomical structure; and
displaying an icon relative to the displayed determined configuration of the anatomical structure representing a location of the instrument relative to the anatomy.

44. The method of claim 36 wherein the first estimate of the anatomical structure, the second estimate of the anatomical structure, or combinations thereof include a definition of tract defined by the diffusion of the matter through the anatomy.

45. The method of claim 36, further comprising:
executing instructions with a processor to automatically select the second criterion.

* * * * *